United States Patent [19]
Carter, Jr. et al.

[11] Patent Number: 5,133,710
[45] Date of Patent: Jul. 28, 1992

[54] THERMAL SEED FOR TREATMENT OF TUMORS

[75] Inventors: Philip S. Carter, Jr., Palo Alto; Frank A. Doljack, Pleasanton, both of Calif.

[73] Assignee: Metcal, Inc., Menlo Park, Calif.

[21] Appl. No.: 442,653

[22] Filed: Nov. 29, 1989

Related U.S. Application Data

[63] Continuation-in-part of Ser. No. 270,843, Nov. 14, 1988, abandoned, which is a continuation-in-part of Ser. No. 169,027, Mar. 16, 1988, abandoned.

[51] Int. Cl.$^5$ .............................................. A61B 17/38
[52] U.S. Cl. ........................................ 606/28; 128/401
[58] Field of Search .................. 606/27, 28; 128/804, 128/401, 422; 600/10, 12, 13, 14; 219/10.75, 33

[56] References Cited

U.S. PATENT DOCUMENTS

| | | | |
|---|---|---|---|
| 1,807,105 | 5/1931 | Schliephaka | 128/804 |
| 3,653,385 | 4/1972 | Burton | 600/10 X |
| 4,545,368 | 10/1985 | Rand et al. | 600/13 X |
| 4,701,587 | 10/1987 | Carter et al. | 219/233 X |
| 4,807,620 | 2/1989 | Strul et al. | 606/28 |

FOREIGN PATENT DOCUMENTS

| | | | |
|---|---|---|---|
| 1284528 | 12/1968 | Fed. Rep. of Germany | 600/10 |
| 0002833 | 10/1981 | World Int. Prop. O. | 128/804 |

OTHER PUBLICATIONS

Brezovich et al, "Effect of Catheters ... Thermoseeds", IEEE, 9th Ann. Conf of the Engine Med. & Biol. Soc., 1987, vol. 3, pp. 1629-1630.
Lilly et al, "Hypertherma induction ... implants", Radiology, vol. 154, No. 1, p. 243, Jan. 1985.
Leonard et al, "Thermoelectric Power ... films", 1976.
Thackray et al, "Indirect heating Source ... " Electrocomponent Sc & Tech., vol. 1, No. 2, pp. 91-96, Dec. 1974.

*Primary Examiner*—Lee S. Cohen
*Attorney, Agent, or Firm*—Howard L. Rose

[57] ABSTRACT

A heater (seed) and system for subjecting body tissue to closely controlled hyperthermia or higher temperatures includes a core of ferromagnetic material having a high resistivity or resistivity of a non-conductor enclosed with a bio-compatible non-magnetic conductive sheath and excited by a coil positioned to establish a magnetic field coupled to the seed. The core is dimensioned so as to reduce demagnetizing effects to acceptable levels. The thickness of the conductive sheath is optimized to maximize heat generation to achieve a heat generating capacity which is considerably greater than that of the bare ferromagnetic material.

21 Claims, 7 Drawing Sheets

THERMAL SEED FOR TREATMENT OF TUMORS

RELATED APPLICATIONS

This application is a continuation-in-part application of application Ser. No. 07/270,843 filed Nov. 14, 1988, now abandoned, in the name of Philip S. Carter which was a continuation-in-part of application Ser. No. 169,027 filed Mar. 16, 1988, now abandoned, in the name of Philip S. Carter, Jr., both for Thermal Seed for Treatment of Tumors.

THERMAL SEED FOR TREATMENT OF TUMORS

The present invention relates to the art of thermal coagulation of human tissue and more particularly to a structure for producing lesions in and otherwise destroying tumors by applying heat thereto.

BACKGROUND OF THE INVENTION

In U.S. Pat. No. 3,653,385 to Charles Burton there is described a method and apparatus for applying heat to body tumors and particularly to brain tumors. The apparatus comprises a needle inserted into the tumor and an r.f. coil located external to the body. The needle consists of electrically conductive ferromagnetic material having a Curie temperature in the range of 150° F. to 200° F.

The frequency of the r.f. source is in the 300 to 400 KHz range and the coil is positioned such that the flux produced by the coil is coupled to the ferromagnetic material. The flux induces a current in the ferromagnetic material and skin effects become involved. The material is heated by the circulating current thus produced.

Needed improvements in the performance of the Burton device include increasing the heating power and making the device bio-compatible, i.e., capable of being inserted in living tissue for extended periods of time.

Recent disclosures by Matsuki and Murakami (H. Matsuki and K. Murakami, "High Quality Soft Heating Method Utilizing Temperature Dependence of Permeability and Core Loss of Low Curie Temperature Ferrite," *IEEE Transactions on Magnetics*, Vol. Mag-21, No. 5, September 1985) and by Matsuki et al (H. Matsuki et al, "An Optimum Design of a soft Heating System for Local Hyperthermia," *IEEE Transactions on Magnetics*, Vol. Mag-23, No. 5, September 1987) describe a needle comprising a ferrite rod and a non-magnetic metal ring into which the ferrite is inserted. An RF coil also located external to the body, produces flux in the ferrite which in turn causes currents to flow in the metal ring. Heat is produced in the ring by these induced currents.

There are numerous problems with the Matsuki et al devices which must be overcome before a practical implant or seed can be realized. The more important deficiencies are set forth. Ferrites are very brittle materials and in order to be used in the environment contemplated by the present invention must be relatively thick; too thick to be useful in tumor treatment of the brain and some other regions of the body. Also due to the thickness required, ferrites provide a poor length to width ratio. The materials used must be bio-compatible but those used in Matsuki et al are not. The total heat transfer is poor because only a part of the surface of the ferrite is enclosed in the ring. The ring is heated and in the region in which it is located transfers heat directly to the tumor. Along those regions of the seed where the ring is not located, heat must be transferred from the ring back into and spread through the ferrite which is a poor heat conductor. Thus efficiency suffers. Also ferrites are not ferromagnetic materials but are ferrimagnetic materials which have lower saturation magnetizations than the ferromagnetics.

Application of ferrites to hyperthermia is possible only if the needle is contained within a mechanically rigid, strong, and non-electrically conductive enclosure. Non-electrically conductive bio-compatible materials have low thermal conductivity, a factor which can seriously degrade the temperature regulating properties of the heater.

A German application, no. P12-84-528.2 published Dec. 5, 1968 for *Device For Elimination of Biological Tissue Through Induction-Heating Objects With Temperatures-Stabilizing Properties* by Dr. Friedrich Forster discloses the use of implant of ferromagnetic material enclosed within a non-magnetic conductor that is compatible with human or animal tissue. Such metal may be gold, silver or other bio-compatible conductive material. The implant is excited by an externally generated magnetic field developed by a current carrying coil or coils. One problem with the Forster disclosure is that it recites a number of parameters that must be considered but gives no idea of what they should be or their interrelationship. Also he uses material of low maximum permeability and between these two problems cannot achieve the desired results without exposing the patient to intense or prolonged magnetic fields.

The present invention makes possible for the first time a practical needle implant device incorporating the features of biological compatibility and effective internal generation and transmission of heat to the surrounding tissue.

BRIEF DESCRIPTION OF THE INVENTION

In accordance with the present invention, a seed structure of high mu material such as with ferromagnetic, ferrimagnetic (under some conditions) or the like material is provided for implanting in body tumors, including brain tumors, which seed requires relatively low energizing fields and low frequencies and which is bio-compatible. A lower energizing field translates into substantially lower power requirements from a supply and less exposure to high intensity magnetic fields of the patient. The use of readily available high mu materials which are quite strong permits seeds to be as small as 1 mm or less in diameter making them suitable for use in the brain. Also such small diameters provide good length to diameter ratios which permit effective permeabilities of at least 100 to be achieved in spite of the demagnetizing effects found in such devices as is discussed subsequently. Bio-compatibility is achieved by coating the surface of the high mu material with a layer of gold, silver or other bio-compatible conductive materials of a specific layer thickness to maximize efficiency. Also the entire surface is coated thus materially improving heat transfer relative to the Matsuki et al devices.

The bio-compatibility feature makes it possible to insert the seed into live tissue without threat to any body organs or functions. This insertion can be accomplished without enclosing the needle in any additional holder or mounting and thus without degrading the temperature self-regulating performance of the needle. In addition, it is possible to have a hole in the needle through which a suture can be threaded. A multiplicity of needles can be mounted on the suture thread and sewn into position in the tumor. Removal of the threaded needles from the body is thereby also considerably simplified.

The mechanism of heating is as follows: the energizing coil produces an alternating magnetic field directed along the axis of the needle. This field produces magnetic flux in the needle core which generates, by means of electromagnetic induction, electric currents in the non-magnetic surface layer and also to some degree in the high mu core. These electrical currents cause resistive heating of the surface layer and the core. These currents also produce an alternating magnetic field which opposes the field applied by the energizing coil. This effect is accounted for by choosing an optimum thickness for the conductive sheath as described below.

When the heater is subjected to a magnetic field, the temperature of the heater rises until near the Curie temperature, $T_c$, the magnetic flux in the core decreases substantially, causing a substantial decrease in the induced currents and the accompanying generated heat. The heater temperature is thereby stabilized at a temperature close to the Curie temperature.

As indicated, gold is one possible choice for the non-magnetic surface layer since it is biologically compatible with living tissue. The thickness of the gold layer is chosen to obtain the maximum heater power. At a 1 MHz frequency this thickness is in the 0.2-0.8 micron range for optimal performance or one micron at 125 KHz. The gold coating can be applied by sputtering or other well known coating techniques. It should be noted that gold has a resistivity not much greater than copper and is thus an excellent conductor of electricity. It is also an excellent thermal conductor.

This sheath thickness of the conductive layer is quite important since, as will be demonstrated subsequently, if the layer is either too thick or too thin the device cannot achieve generation of maximum power.

This concept can be understood qualitatively as follows: if the conductive sheath layer is very thin its resistance is very high. The corresponding electrical power generated in the sheath layer is very low since the high resistance of the layer prevents much current from flowing. As the sheath layer thickness is increased, its resistance decreases causing the current and the corresponding power to increase. Simultaneously however, it has been found that the sheath current produces an alternating reactive field which opposes the applied energizing field produced by the coil. This reaction field builds up as the sheath layer thickness increases. An optimum thickness is reached at which a further increase in thickness causes the sheath power to decrease. A formula for an optimum thickness is developed subsequently.

Demagnetizing effects related to the length-to-diameter ratio of the seed must also be considered. To render such effects minimal the length-to-diameter ratio should be of the order of ten and preferably 20. If, for instance, a seed having a ratio of thirteen is provided, an intrinsic permeability of 300 is reduced to about 70, and one of a permeability of 600 is reduced to about 100, both still useful values.

Even with the demagnetizing effects inherent in the structure of the present invention, permeabilities of approximately 70 and better are readily maintained and are suitable for the purpose contemplated herein, the higher effective permeabilities, of course, being preferable.

The seed of the present invention has a core of relatively high resistivity high mu alloy material of appropriate Curie temperature. Some of the suitable materials and their Curie temperatures are:

| Material | $T_c$ |
| --- | --- |
| Carpenter TC30-2 alloy $\approx$30% Ni, $\approx$70% Fe | $\approx 55°$ C. |
| Nickel + 29.6 wt. % copper | $\approx 50°$ C. |
| Nickel plus various percentages of palladium | $\approx 50$-$58°$ C. |
| 33-43% nickel, 10-15% Cr and 0.3% Si | $\approx 50°$ C. |

The core is surrounded by a low resistivity material such as gold. The combination of a low resistivity non-magnetic layer, a high resistivity alloy core and energizing coil has rough similarities to the case of a transformer. The conductive layer is analogous to a single turn secondary winding of a transformer in which the winding is short circuited. The ferromagnetic core is analogous to the transformer core. The analogue of the primary winding is the energizing coil.

OBJECTS OF THE INVENTION

It is an object of the present invention to provide a device for insertion into a body to destroy body tissue, which device maximizes efficiency.

It is another object of the present invention to insert into tissue to be destroyed in a biological body, a heater comprising a poorly conductive high mu material coated with a relatively conductive, bio-compatible, non-magnetic material, the length to radius ratio of the heater and thickness of the conductive coating being chosen to maximize efficiency of the heater.

BRIEF DESCRIPTION OF THE DRAWINGS

FIG. 13 illustrates an arrangement of energizing coils and a power supply for energizing an arbitrarily oriented needle;

DETAILED DESCRIPTION OF THE DRAWINGS

Figure 1:
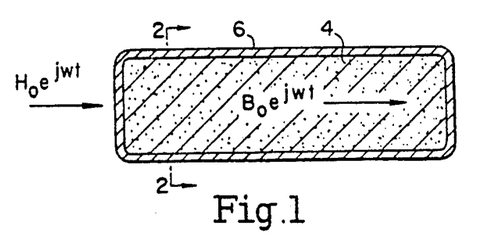
FIG. 1 is a view in longitudinal cross section of a seed according to the present invention.
Figure 2:
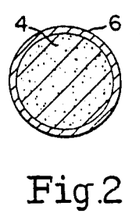
FIG. 2 is a view in transverse cross-section of the seed of FIG. 1.

Referring now to FIGS. 1 and 2 of the accompanying drawings there is illustrated a first embodiment of the present invention. A seed 2 includes a cylindrical core 4 of high resistivity high mu material substantially completely enclosed within a coating 6 of low resistivity biologically inactive material such as copper, silver or gold.

Figure 3:
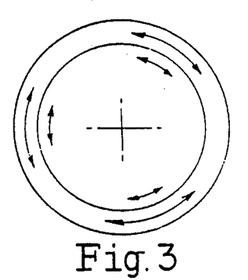
FIG. 3 is a transverse view of the section of FIG. 2 indicating current flows.

When subject to an axial ac magnetic field $H_o e^{j\omega t}$, a flux of value $B_o e^{j\omega t}$ is induced in the core 4. The induced flux produces current flow primarily in the coating 6; the current flow following the paths illustrated in FIG. 3.

Figure 4:
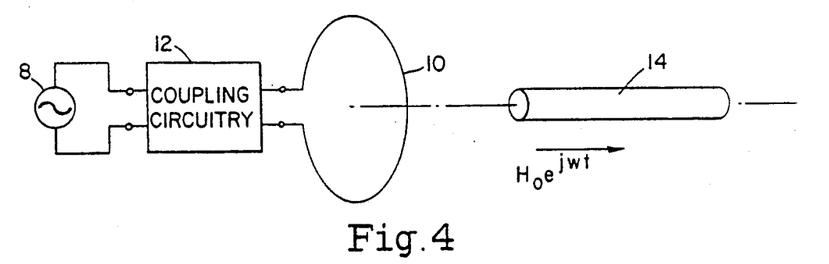
FIG. 4 illustrates the positioning of a seed in the field produced by an exciting coil.
Figure 5:
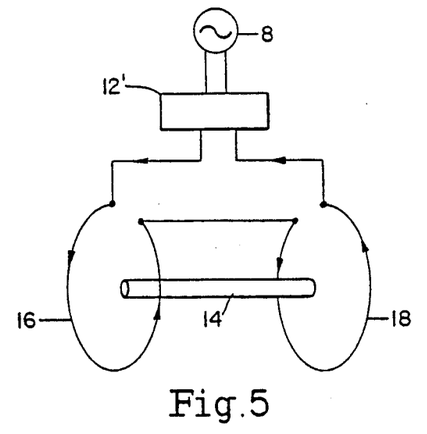
FIGS. 5 and 13 illustrate further coil arrangements which may be employed with the present invention.

The field may be induced by a single coil arrangement as illustrated in FIG. 4 or a Helmholtz coil arrangement as illustrated in FIG. 5. The single coil arrangement includes an ac source 8 at the appropriate frequency, a coil 10 and a network 12 efficiently coupling the source to the coil. The coil 10 is circular and is approximately coaxial with a heater 14 which may be of the type illustrated in FIG. 1 of the accompanying drawings.

Figure 13:
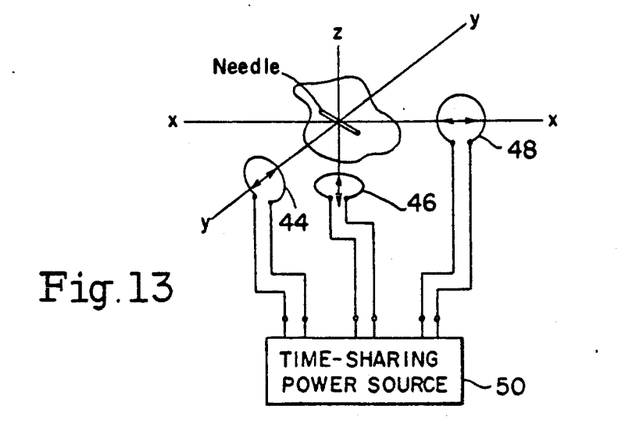

The induced flux $B_o e^{j\omega t}$ is maximum when the major axis of the needle is parallel to the energizing field $H_o e^{j\omega t}$. On or near the coil axis, $H_o e^{j\omega t}$ is nearly parallel to such axis, thus $B_o e^{j\omega t}$ is maximized when the needle is parallel or nearly parallel to the coil axis. However, useful coupling to the needle when the angle between the needle axis and the field direction is as large as 45 degrees is possible but see FIG. 13.

The loop or loops may also be rectangular, or have an elliptical shape, in order to achieve the desired distribution and direction of the energizing field. The loops can even be bent into non-planer shapes which are conformable to the shapes of the body region being treated to produce better coupling between the coil and seed. The optimum coil shape and size for a specific situation can be arrived at experimentally or by calculation. Calculations are considerably simplified using magnetic computer design aids, e.g., Westinghouse's WEMAP, which are now widely available.

The Helmholtz arrangement of FIG. 5 is useful where the distance from a single coil as in FIG. 4 may be sufficiently great that the field becomes non-uniform or skewed along the axis of the heater. The Helmholtz coils 16 and 18 which are approximately coaxial with the heater 14 maintain a much more uniform field at the heater location when it is about midway between the coils. The coupling network 12' is somewhat different from that of FIG. 4 due to the two coils but serves the same purpose.

Theoretical calculations were made of the current distribution in a computer simulation of the heater shown in FIGS. 1 and 2. The approximation model used in this simulation is illustrated in FIG. 6 as a two dimensional infinitely long model.

Figure 6:
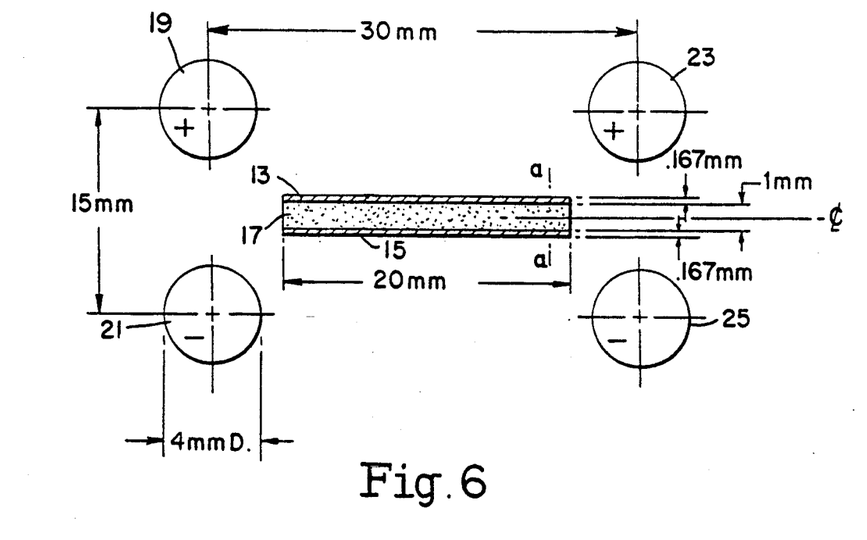
FIG. 6 is an idealized model of the needle and induction coils.

In FIG. 6 the sheathed cylindrical heater of FIG. 1 is simulated by a three layer strip of infinite length. The top and bottom layers 13 and 15, respectively, represent the sheath. The core 17 of the cylindrical heater is simulated by the central layer of the three layers. The Helmholtz coil is simulated by the four infinitely long circular copper rods, 19, 21, 23 and 25, the two upper rods carrying currents equal to but in the opposite direction from the currents in the lower rods. The magnitude of the current in each rod was specified to be 1 ampere. The relative permeability of the simulated core in FIG. 6 is 1000. The core conductivity is $1.25 \times 10^6$ mho/meter. The sheath thickness is 0.167 mm and is copper with a conductivity of $0.5 \times 10^8$ mho/meter. Thus the ratio of conductivities is 40:1. The core thickness is 1 mm and the width is 20 mm. The 20 mm width corresponds to a 20 mm length of cylindrical heater. The frequency of the coil current is 70.5 KHz.

Figure 7:
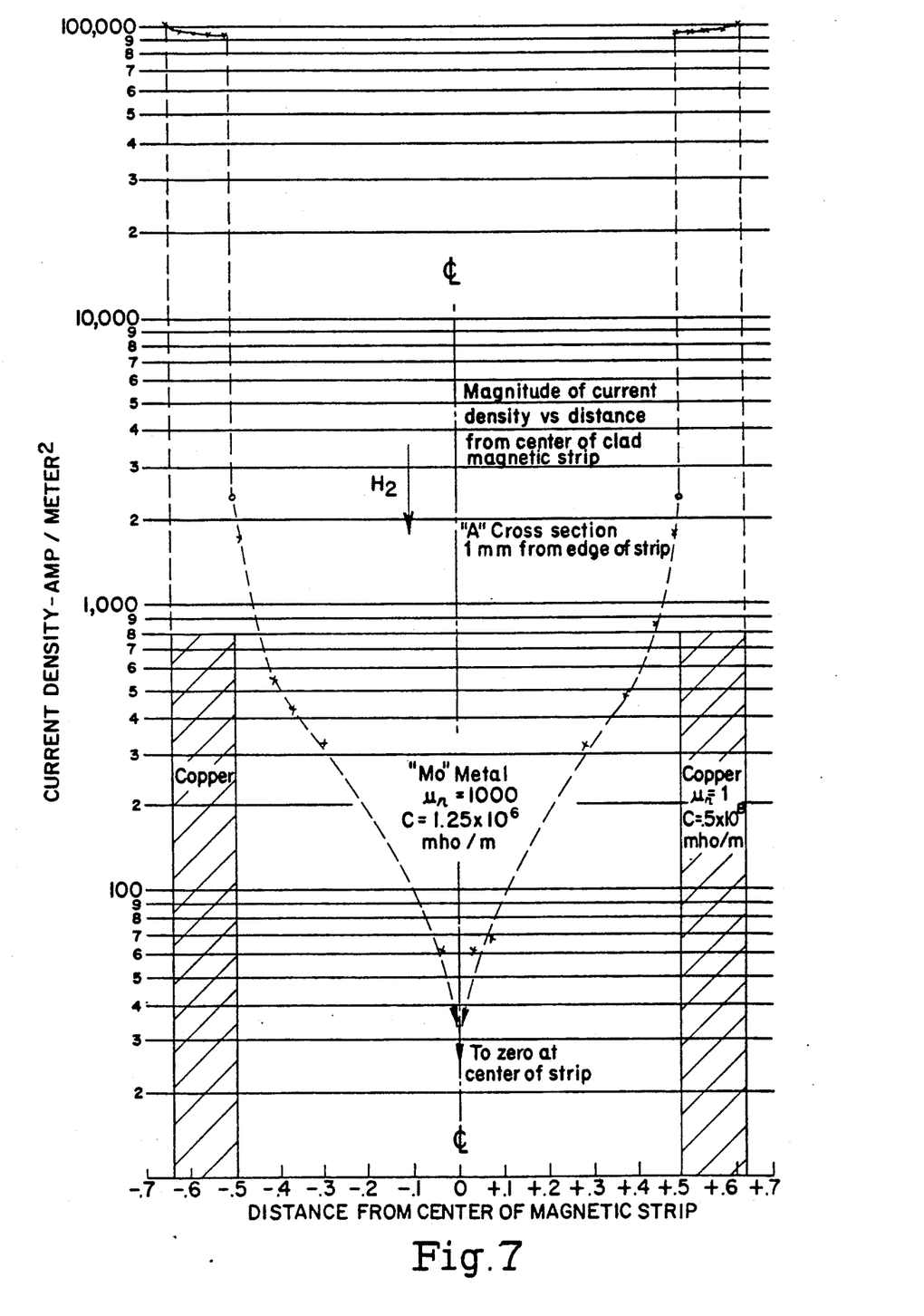
FIG. 7 is a graph indicating the current distribution in the device of FIG. 6.

Referring to FIG. 7 of the accompanying drawings, there is illustrated a graph of the calculated theoretical current density distribution in the simulated heater of FIGS. 1 and 2 as illustrated in FIG. 6. The abscissa, current density, has a value of zero along the axis of the heater and extends to the left and right to represent radial positions outwardly from the core center. The current density is the left scale ordinate ranging from 10 to 100,000 amps/meter$^2$.

At the interface between the copper and the core, the ratio of current densities in the copper and the core is equal to the ratio of the conductivities, 40:1. This fact is illustrated in FIG. 7 where the current density in the core at the interface is about 2400 amps/meter$^2$ and in the copper is about 97,000 amps/meter$^2$. The current density in the sheath rises still further outwardly from the interface as is also apparent from the graph.

As was stated above, the achievement of maximum power output requires the use of a specific optimum thickness for the conductive surface layer. Thus thickness can be estimated by means of theoretical calculations or determined experimentally. Two theoretical approaches are developed here. The first is a simple formula based on Faraday's Law which requires the assumption that the high mu core material is non-conductive. The second is based on an idealized computer model and is presented below.

Figure 8:
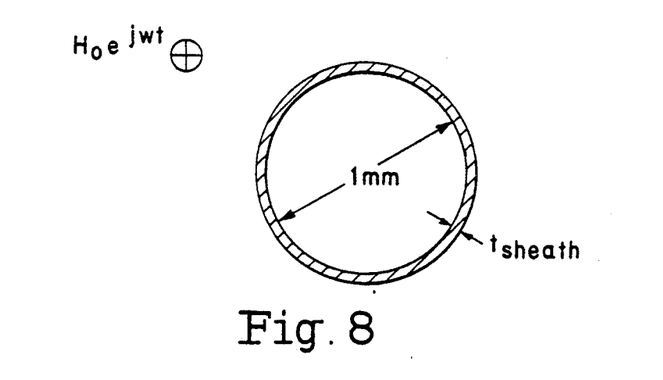
FIG. 8 illustrates a cross-section of an idealized needle model used to calculate optimum surface layer thickness.

Using a theoretical approach, a general formula for optimum sheath thickness is developed as follows with reference being made to the needle illustrated in FIG. 8 of the accompanying drawings:

Using Faraday's Law:

$$\epsilon = -\frac{d}{dt}(\phi_1 + \phi_2)$$

ti where $$\phi_1 = \pi r^2 B_o e^{j\omega t} = \pi r^2 \mu_e H_o e^{j\omega t}$$
$$\phi_2 = \pi r^2 B_J = \pi r^2 \mu_e H_J$$

where
$B_o$ is applied magnetic field
$l$ is length of needle
$\epsilon$ is induced voltage
$J$ is sheath current density
$j$ is the imaginary number $\sqrt{-1}$
$\phi_1$ is magnetic flux due to applied field
$\phi_2$ is magnetic flux due to current in sheath, and
$t^1$ is sheath thickness.
$t$ is time
$r$ is the radius of the needle The following assumptions are made $t^1 << r$ $l >> r$, and no current flows in the core.
By Amperes' Law:

$H_J l \sim I \sim J t^1 l \rightarrow H_J \sim J t^1$

Also $J \sim \sigma \dfrac{\epsilon}{2\pi r} \rightarrow H_J = \dfrac{\sigma t^1}{2\pi r} \epsilon$ where $\sigma$ is sheath conductivity.

$\phi_2 \sim \frac{1}{2} r \mu_e \sigma t \epsilon$

Substituting in Faraday's Law and reducing $\epsilon \sim \dfrac{2\pi r^2 \mu_e \omega H_o}{-\omega \mu_e \sigma r t^1 + 2j} e^{j\omega t}$ Power $\sim \frac{1}{2} \dfrac{\epsilon \cdot \epsilon^*}{\frac{2\pi r}{\sigma t^1 l}}$ which reduces to $P \sim \frac{1}{2} \left[ \dfrac{\omega \mu_e r t^1 \sigma}{(\omega \mu_e r t^1 \sigma)^2 + 4} \right] (2r^2 \mu_e \omega l H_o^2)$ The expression in brackets is of the form $\dfrac{X}{X^2 + 4}$ which has a maximum when $X = 2$.
Thus at maximum power $\sigma_{Pmax} \sim \dfrac{2}{\omega \mu_e r t^1}$ and $P_{max} \sim \frac{1}{2} r^2 \mu_e \omega l H_o^2$ Thus the maximum rate of energy transfer is proportional to the magnetic energy density ($\mu_e H_o^2$), the frequency ($\omega$) and the volume of the seed ($\sim r^2 l$), assuming as started above, that $t^1 << r$ and $r << l$.

It is apparent that to maintain $\sigma$ at a given value frequency must increase if core size or sheath thickness decreases and visa versa.

In addition to the above approach, a theoretical idealized model of the needle was used to calculate the generated power in the needle using a computer program. The idealized computer model used in these calculations, and illustrated in FIG. 8, was an infinitely long high permeability circular cylinder with a thin surface layer of non-magnetic conductive material. An axial AC energizing field having a magnitude of 25 oersteds and a 1 MHz frequency was assumed.

The theoretical analysis of this model was performed using the computer programs, MESHMAKER 4.0 and EDDY XY 4.0, developed and furnished by the Ansolft Corporation, Pittsburgh, Pa. These programs are based on finite element numerical approximation procedures.

An explanation of this method and its application to electromagnetics problems is given in "What Every Engineer Should Know about Finite Element Analysis," edited by John R. Brauer, Marcel Dekker, Inc., N.Y. (1988).

Figure 9:
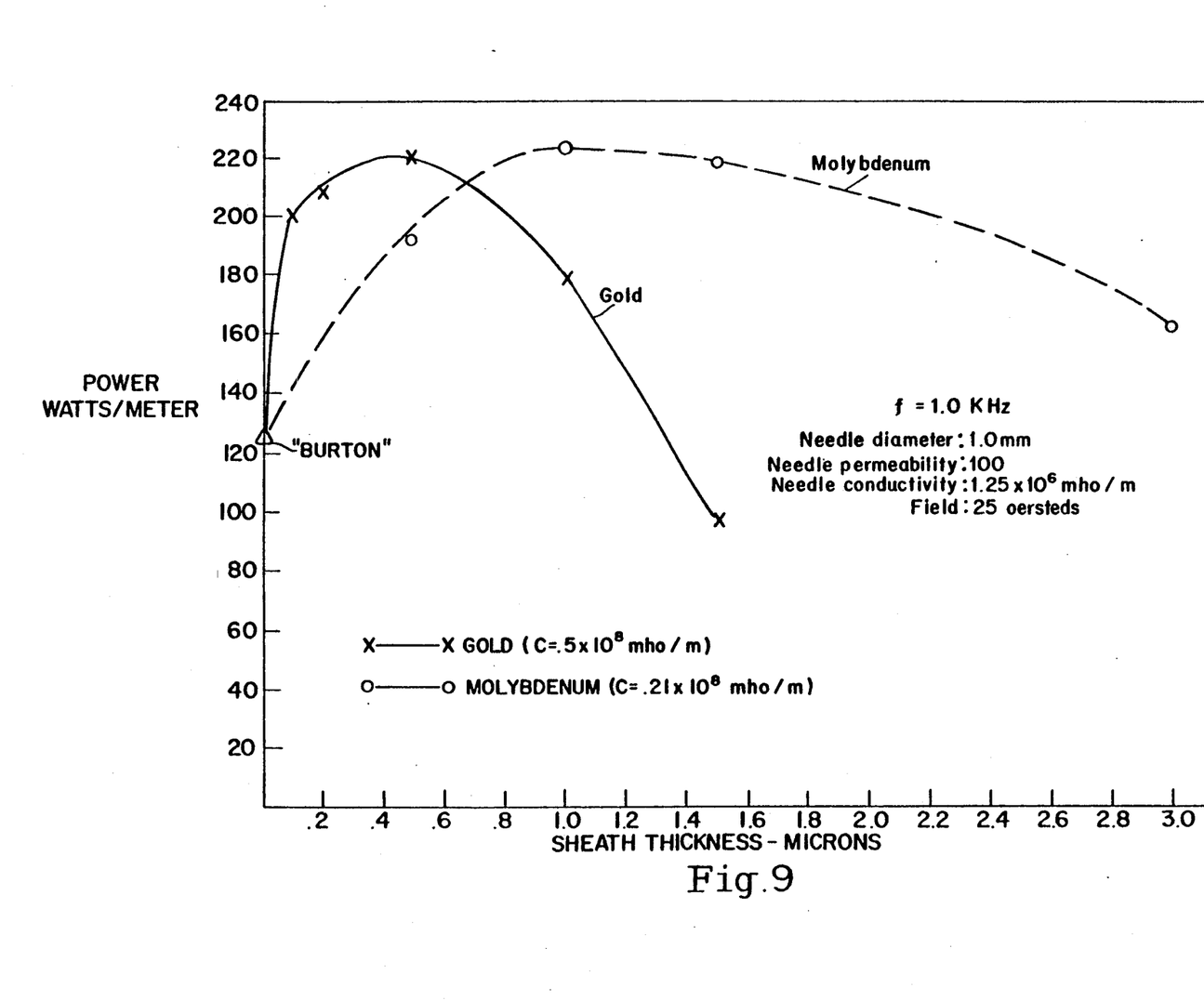
FIG. 9 is a graph of power vs. surface layer thickness.

A needle diameter of 1 mm was chosen. The effective permeability of the core was assumed to be 100, and the core conductivity assumed to be $1.25 \times 10^6$ mho/meter, a typical conductivity of the ferromagnetic material employed. Two different surface layer materials were chosen: gold, for which a conductivity of $0.5 \times 10^8$ mho/meter was assumed, and molybdenum, for which a conductivity of $0.21 \times 10^8$ mho/meter was assumed. The power per unit length generated at a frequency of 1 Mhz was calculated for these two sheath materials as a function of the thickness of the sheaths. The results of these power vs thickness calculations are shown in FIG. 9. An optimum thickness occurs at which maximum power is generated. As expected the magnitude of the maximum power is the same for both materials and the optimum thickness is substantially larger for the molybdenum than for gold because molybdenum has a lower (by a factor of about 2.5) conductivity than gold. Further increases in the optimum surface layer thickness can be obtained by using other bio-compatible material such as titanium, platinum and 316 stainless steel. Approximate optimum surface thicknesses for some of these materials were calculated based on the following approximate formula.

$$\text{Optimum thickness} = \dfrac{\text{Optimum thickness of gold} \times \text{Resistivity of candidate material}}{\text{Resistivity of gold}}$$

| Material | Approximate Thickness - microns |
|---|---|
| Platinum | 2.2 |
| Titanium | 27 |
| 316 Stainless Steel | 15 |

Figure 10:
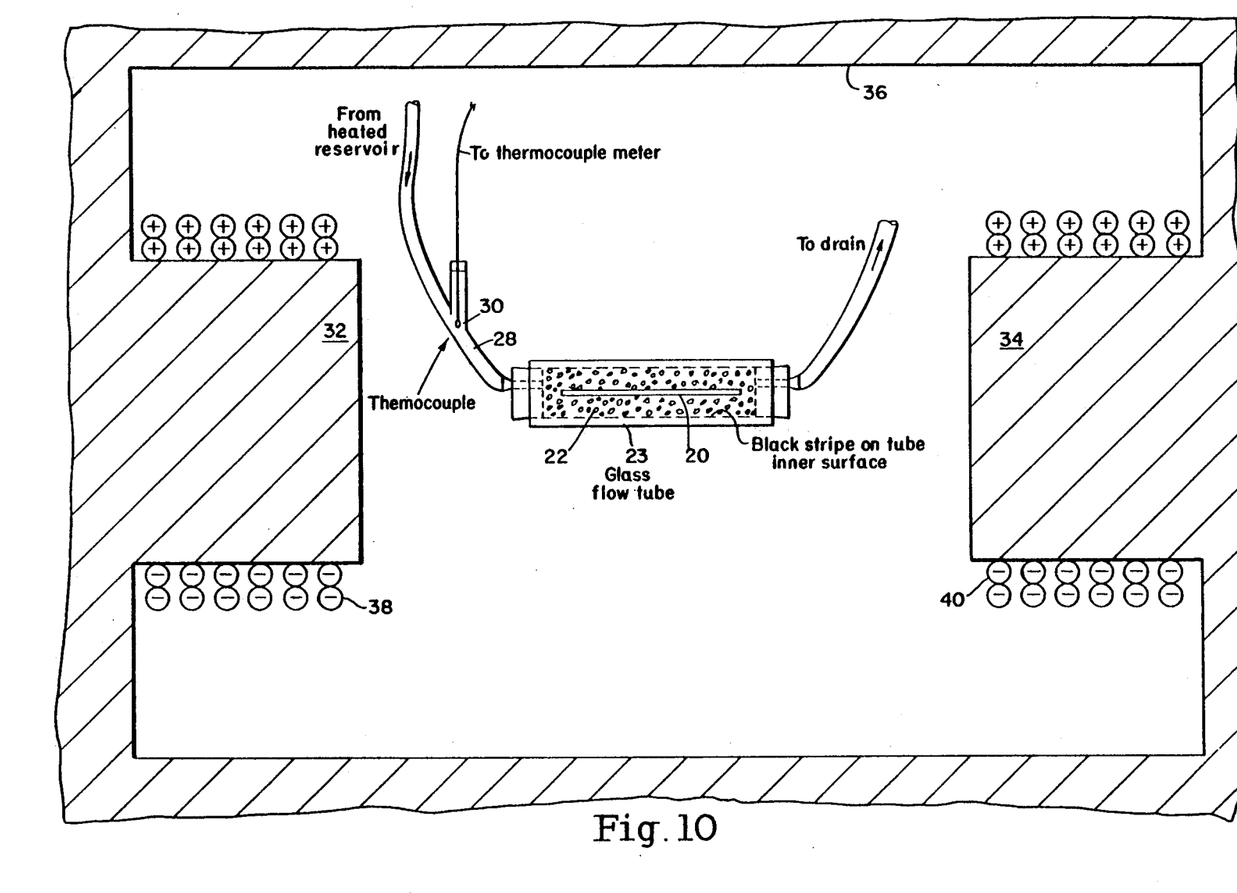
FIG. 10 illustrates a test setup for testing a seed of the present invention.
Figure 11:
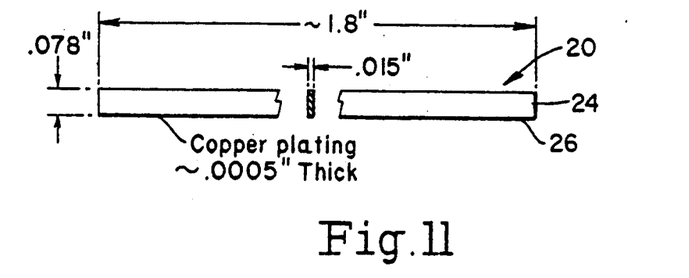
FIG. 11 illustrates the seed of FIG. 8 with dimensions.

In order to test a heater in a simulated environment, the apparatus of FIG. 10 was assembled. A needle 20 was embedded in ordinary cellulose sponge material 22 in a tube 23, the sponge material simulating tissue. The needle, see FIG. 11 has a magnetic core 24 of Carpenter TC30-2 alloy, annealed before plating for thirty minutes at a temperature of 800° C. A non-magnetic conductive sheath 26 of copper (conductivity close to gold and cheaper) was electroplated on the core to a depth of about 0.0005 inch or 12.7 microns which is less than one skin depth at 1 MHz. No attempt was made to optimize the thickness of the copper, the experiment being conducted strictly for the purposes of testing operability of the system. The seed was 1.8 inches long, 0.015 inch thick and 0.078 inch wide. The glass tube was 2.4 inches long with an I.D. of 0.45 inch and an O.D. of 0.55 inch.

Returning to FIG. 10, water was introduced into the tube 23 through tube 28 at a temperature of about 37° C. by means of an external heater, not illustrated. A thermocouple 30 was located in the tube 28 and was connected to a heater control unit to maintain the temperature of the water entering the tube as closely as possible to 37° C. Some small variations occurred as flow rates were varied; becoming cooler at slow flow rates due to conductive and convective cooling in the tube 28.

The tube 23 was placed between poles 32 and 34 of a ferrite core 36 having coils 38 and 40 wound around the poles 32 and 34, respectively.

The test was conducted with 2.6 amps RMS provided to the coils at 70.5 KHz. The two coils had 96 turns total and the gap between the poles 32 and 34 was 2.7 inches. This structure provided an axial field of approximately 45 oersteds to the needle 20.

To calibrate the needle it was initially painted black and mounted loosely on a piece of polystyrene foam. With the needle cooled only by the surrounding air and with the coils energized as stated above the regulated temperature of the needle was measured, using an optical pyrometer, at 53° C.

The temperature of the simulated tissue was measured as follows using the optical pyrometer. A narrow stripe of black paint was applied to the inside surface of the glass tube so that it was in direct thermal contact with the cellulose simulated tissue. The optical pyrometer was focused on this black stripe. The accuracy of this scheme of measuring through glass had been confirmed in advance by a similar pyrometer measurement of the temperature of water in a glass beaker, the temperature of which was measured by a thermocouple immersed in the water.

To start the test, the water flow rate was regulated at a maximum flow rate of 250 milliliters per hour corresponding to 1.4 milliliters per minute per gram of tissue which is similar to maximum blood flow rates in healthy human tissue. The needle was next located as indicated in FIG. 8 and a first test conducted. The temperature stabilized at 51° C. The flow rate was next reduced to 5 ml/hr. and the temperature remained constant. The current to the coil was then reduced by a factor of about 1.4, thus reducing power by a factor of 2. The temperature declined 2° C. to 49° C. The flow rate was then raised to 250 ml/hr. and the temperature increased by about 1° C. to 50° C. These data are set forth in Table I below:

TABLE I

| Flow Rate | Current in AMPS | |
|---|---|---|
| | 2.6 | 1.4 |
| 250 ml/hr | 51° C. | 50° C. |
| 5 ml/hr | 51° C. | 49° C. |

When the coil current and flow were returned to 2.6 amperes RMS and 250 ml/hr., respectively, the temperature returned to 51°C.

Thus it is apparent that the design of the seed is fully adequate to maintain temperature at a desired level in the human body.

Figure 12:
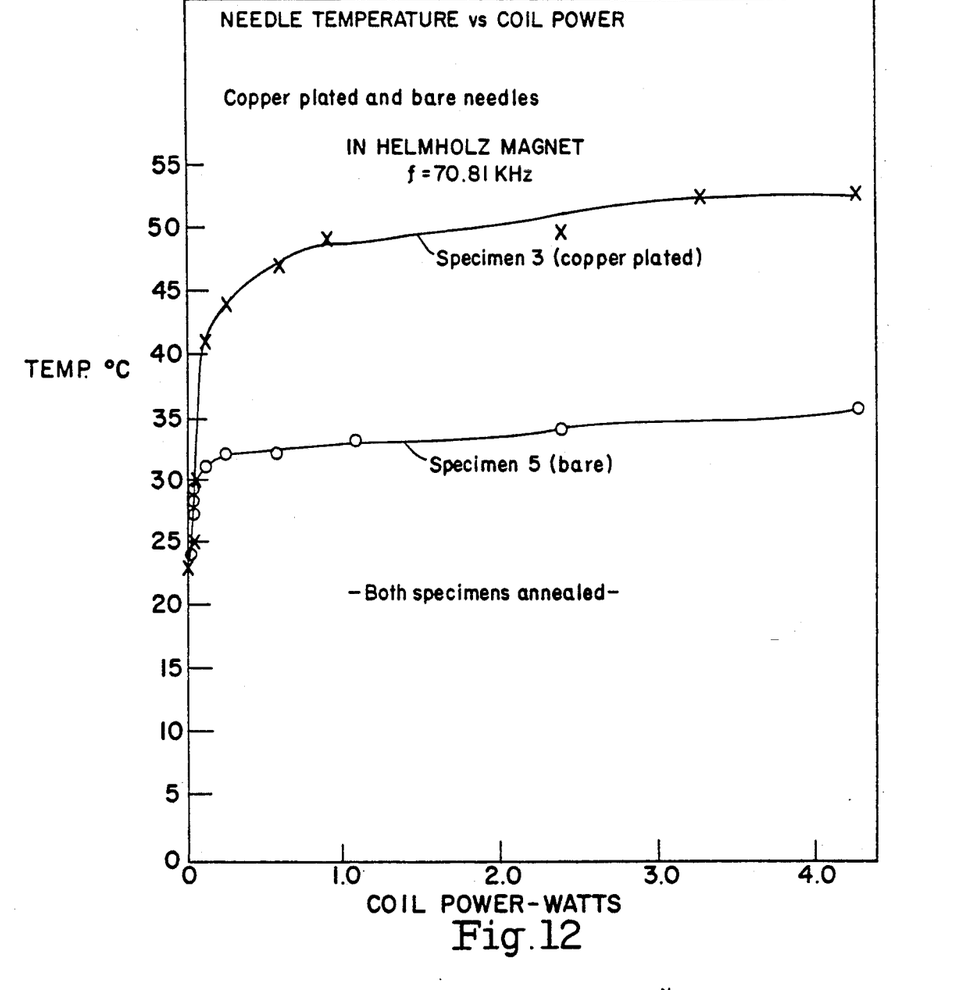
FIG. 12 illustrates a graph comparing the wattage required to reach Curie temperature of a sheathed as opposed to a bare heater.

Referring now to FIG. 12 of the accompanying drawings there is illustrated graphs of a specimen (5) not having copper cladding and a specimen (3) with copper cladding. It is noted that the clad specimen has reached Curie temperature, approximately 52.5° C., with 4 watts input while the unclad specimen is still well below Curie temperature at about 36°C. with a 4 watt input to the energizing coil. The specimens were of the same size and shape and of the same ferromagnetic material, TC30-2, the clad specimen having a copper sheath of 0.0005". The specimens were mounted on foam plastic in an air environment.

The coil arrangement of FIGS. 4 and 5 operate well where the orientation of the needle can be precisely determined and for coils located as required. When the orientation of the needle is not known precisely or the coils cannot be located properly, it may be necessary to utilize the coil arrangement of FIG. 13. This arrangement employs three coils 44, 46 and 48. The three coils are set at right angles each to the other two. The coils are energized one at a time in a repetition sequence by a standard time sharing power source 50. In consequence regardless of orientation the seed is subject to full field strength at least during one-third of each cycle of the source.

Figure 14:
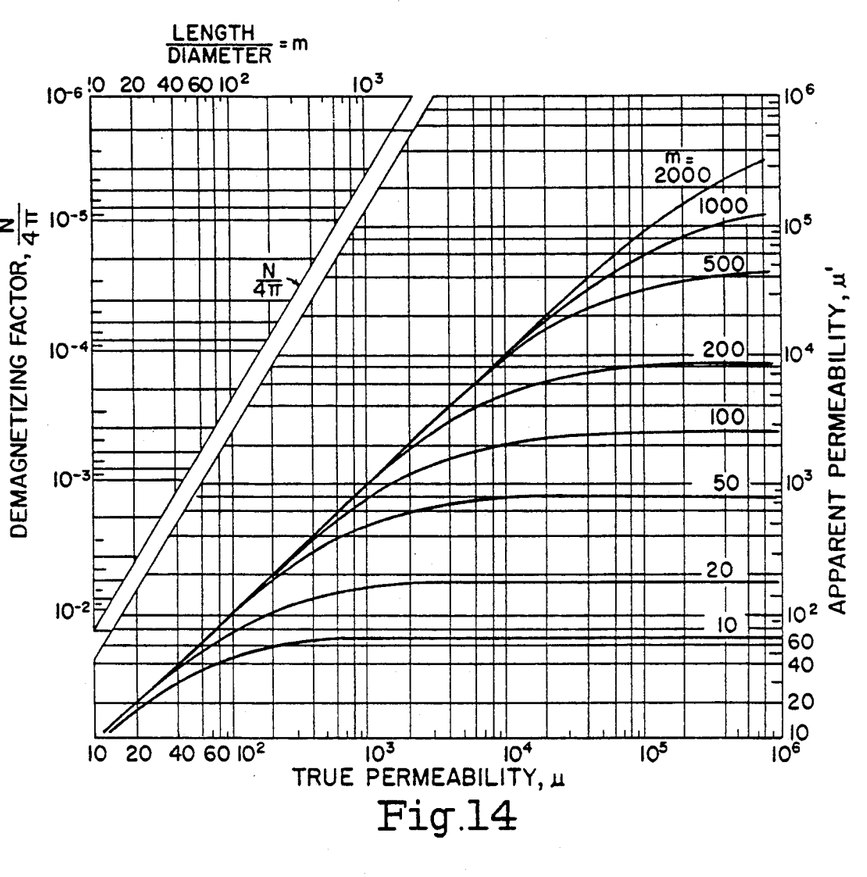
FIG. 14 illustrates a graph indicating the change in effective mu, $m_e$ with changes in the length to thickness ratio of a ferromagnetic member.

As has been previously stated, the length to current diameter ratio of the seed should preferably be at least 10:1 and preferably 20:1 to maintain demagnetizing field at an acceptable level. In this context reference is made to the graphs of FIG. 14 of the accompanying drawings which is taken from Page 848, of the book *Ferromagnetism*, by Bozorth, D. Van Nostrand Co., Inc., N.Y. A reference to the graphs readily demonstrates that with the ratio m=20, the maximum apparent permeability of a material having an intrinsic permeability of 10,000 to 1,000,000, is about 180. A material with a true permeability of 400 has an apparent permeability of about 120.

The seeds thus far described have the core and sheath in direct electrical and thermal contact. In some instances the material of the sheath and core may be such that one of the materials diffuses into the other. This problem may be overcome by placing a barrier between the two materials that is highly heat conductive, but does provide a physical barrier between the materials. Flash nickel in either its ferromagnetic or paramagnetic form may be employed for such a purpose. A few microinches of such material are usually sufficient and thus vapor deposition, sputtering and like processes may be employed. The barrier may be electrically conductive or non-conductive so long as it is thermally conductive.

Figure 15:
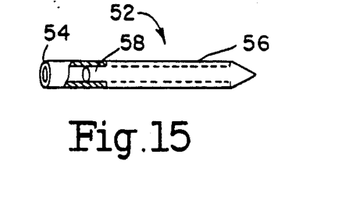
FIG. 15 illustrates one means for connecting a seed to a needle.

Referring now specifically to FIG. 15 of the accompanying drawings, there is illustrated a needle with the heater of the present invention located at the end thereof. Specifically, a needle 52 includes a non-heat conductive hollow cylinder 54 with a heater 56 of the present invention having a cylindrical projection 58 of reduced diameter at its proximate end. The projection 58 is force fitted or otherwise secured in the open end of member 54. The heater is of a type as disclosed herein and thus may be inserted into the body of the patient and, guided by fluoroscopy or related tracing techniques, inserted into a tumor to be treated.

Figure 16:
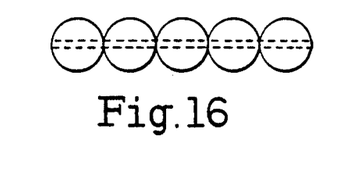
FIG. 16 illustrates an advantageous arrangement of special "needles".

The preferred embodiments of the invention described herein are all cylindrical in shape since for most purposes this is the desired shape both from the point of view of insertion into the body and maintaining a proper ratio for maintaining relatively high effective permeabilities. Other shapes may be employed where dictated by a specific use. Thus a spherical or elliptical shape may be required. A spherical seed has an effective mu of about 3. The effective permeability of spheres and relatively short ellipsoids can be increased by placing them close together or in contact with one another as illustrated in FIG. 16 for the case of spherical "needles." This arrangement can be implemented very practically by introducing holes in the individual spheres through which a suture is threaded.

Although it is strongly preferred that a constant current source be employed, due to the loose coupling of the coil to the needle a non-constant current source may be employed in some applications. A current deviation of ±5% of the nominal current is acceptable; this representing a power deviation of ±10%. A constant current source, Model No. AI-FP-2.5-200 equipped for constant current output at 80-200 MHz, is manufactured by ENERCON Industries Corporation.

The Curie temperature employed in these devices is not necessarily the absolute Curie temperature but the temperature at which the high mu material approaches paramagnetism to the extent necessary to achieve the purposes of this invention. Such temperature which is called herein the "effective Curie temperature" may be as little as 1° C. or as great as 100° C. different from absolute Curie temperature depending upon the material.

Other improvements, modifications and embodiments will become apparent to one of ordinary skill in the art upon review of this disclosure. Such improvements, modifications and embodiments are considered to be within the scope of this invention as defined by the following claims.

We claim:

1. A heater system for subjecting body tissue to hyperthermia or higher temperatures comprising
a heater including a core of high mu material of low electrical conductivity having an elongated dimension, a sheath of electrically conductive material substantially completely covering said core and having a permeability of more than an order of magnitude less than the permeability of said core,
a coil structure for producing an alternating magnetic field,
means for locating said coil structure relative to said heater to induce a current therein,
said means including means for connecting said coil structure across a source of current alternating at a frequency of at least radio frequencies,
said core having dimensions transverse to said elongated dimension in a range of one-tenth and less than that of the elongated dimension,
said sheath being of a thickness to produce maximum power dissipation in said sheath.

2. A heater system for subjecting body tissue to hyperthermia or high temperatures comprising
a heater including a cylindrical core of high mu material of low electrical conductivity having an elongated dimension, a sheath of electrically conductive material covering all but the ends of said core and having a permeability of more than an order of magnitude less than the permeability of said core,
a coil structure for producing an alternating magnetic field,
means for locating said coil structure relative to said heater to induce a current therein,
said means including means for connecting said coil structure across a source of current alternating at a frequency of at least radio frequencies,
said core having dimensions transverse to said elongated dimension in a range of one-tenth and less that of the elongated dimension,
said sheath having a thickness of one skin depth or less at the frequency of operation of said system.

3. A heater system according to claim 1 or claim 2, further comprising
a needle,
said heater located at one end of said needle.

4. A heater system according to claim 2 wherein said sheath is chemically inert.

5. A heater system according to claim 2 wherein the material of said sheath is bio-compatible.

6. A heater system according to claim 1 or claim 2 wherein said coil structure is a Helmholtz coil system.

7. A heater system according to claim 1 or claim 2 wherein said coil structure includes three mutually perpendicular coils.

8. A heater system according to claim 7 further comprising
means for sequentially and successively applying said alternating current to said coils.

9. A heater according to claim 1 wherein said core has a resistivity at least 10 times the resistivity of said sheath.

10. A heater according to claim 1 wherein said core has a resistivity of at least 100 times that of said sheath.

11. A heater system according to claim 1 or claim 2 wherein the sheath is gold.

12. A heater system according to claim 11 including means for providing power to said heater from a source of current, the power delivered per unit length of heater vs sheath thicknesses for gold is defined by the graph of FIG. 9 for current frequencies of one megahertz.

13. A heater system according to claim 1 or claim 2 wherein the sheath is silver.

14. A heater system according to claim 1 or claim 2 wherein said sheath thickness is determined approximately by the formula $$T = T_1 \frac{R}{R_1}$$

where
T is optimum thickness for candidate material
$T_1$ is optimum thickness for gold
R is candidate metal resistivity
$R_1$ is resistivity of gold.

15. A heater system according to claim 1 or claim 2 wherein said coil structure is shaped to produce a maximum magnetic field parallel to the axis of the heater.

16. A heater system according to claim 1 or 2 wherein the effective permeability, radius and length of the heater, the conductivity and thickness of the sheath and the strength of the magnetic field produced by the coil when energized are defined as follows:

$$\sigma_{Pmax} \sim \frac{2}{\omega \mu_e r t^1}$$

and $$Pmax \sim \tfrac{1}{2} r^2 \mu_e \mu l H_o^2$$

where
$\sigma$ is sheath conductivity
$t^1$ is sheath thickness
$\omega$ is $2\pi f$
$\mu_e$ is effectively permeability
r is radius of the heater
l is length of the heater
$H_o$ is magnetic field strength.

17. A heater system according to claim 1 or claim 2 wherein said alternating field is produced by a constant alternating current.

18. A heater system according to claim 1 or claim 2 further comprising
a plurality of said cores each with a hole therethrough,
a suture,
said cores being strung on said suture.

19. A heater system according to claim 1 or claim 2 wherein, said sheath is gold with a thickness of approximately 0.3 microns at a frequency of approximately one megahertz.

20. A heater system according to claim 1 or claim 2 wherein said sheath is molybdenum, means for providing power to said heater from a source of current, the power delivered by said heater per unit length of heater when connected to a source of power vs. sheath thickness being defined by the graph of FIG. 9 for frequencies of one megahertz.

21. A heater system according to claim 1 or 2 wherein said core is a ferromagnetic material having a resistivity at least 10 times that of said sheath.

* * * * *